Aug. 30, 1932. B. W. KEITH ET AL Plant Pat. 26
STRAWBERRY
Filed Sept. 3, 1931
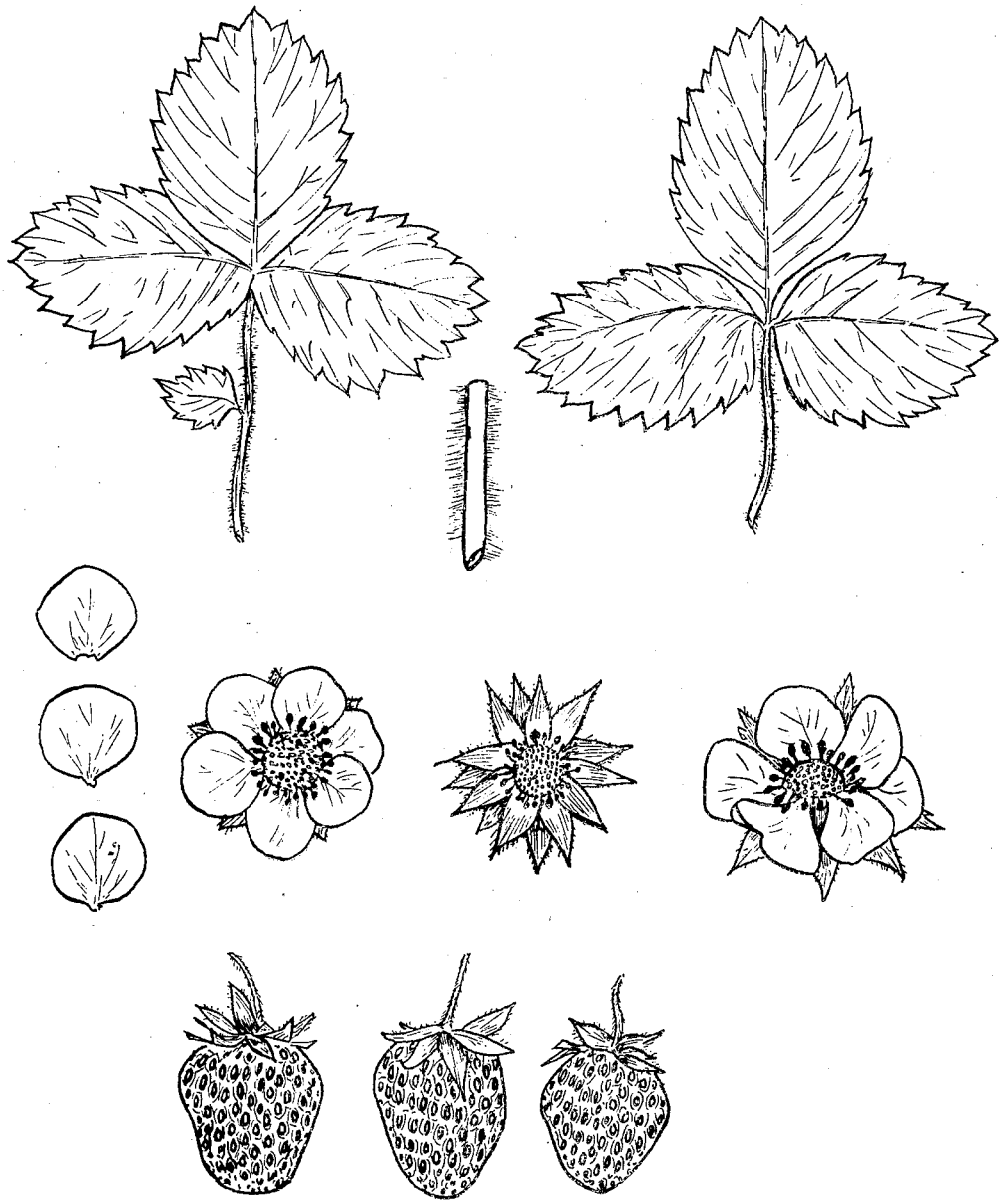
Bert W. Keith
Bud W. Keith
INVENTORS.

Patented Aug. 30, 1932 Plant Pat. 26

UNITED STATES PATENT OFFICE

BERT W. KEITH AND BUD H. KEITH, OF SAWYER, MICHIGAN

STRAWBERRY

Application filed September 3, 1931. Serial No. 560,919½.

This new variety of spring (June) strawberry is a chance seedling of the Glen Mary variety of spring (June) strawberry. It was taken up in early June, 1926, from the edge of a two-year Glen Mary fruiting row with other small seedlings when each seedling did not have more than three small leaves and transplanted in a cold frame, grown therein for one year and then planted in a test plot where its characteristics, as a worthy commercial variety, were first noted. It has been tested and grown in fruiting rows during the spring strawberry seasons of 1929, 1930 and 1931. Its long fruiting season, its uniform size, color and firmness of berry are such as to warrant it being listed as a new worthy variety of spring fruiting strawberry.

*Brief description*

Spring, or June-bearing variety with dark green foliage, berries conic to blunt conic, medium uniform size, solid bright lasting glossy red inside and out. Plant upright to spreading; leaflets slightly crimped;—plant healthy, hardy, producing runners freely.

*Detail description*

*Plant.*—Medium to large, six to eight inches high, single crown (rarely double), vigorous, hardy;—foliage dark glossy green, healthy, medium to coarse, abundant, somewhat spreading, mostly upright, practically free from leaf spot (*Mycosphærella fragariæ*);—makes runners freely.

*Roots.*—Fibrous, tough, abundant, medium long, 6 to 8 inches in average fertile soil, not wiry.

*Leaves.*—Medium to large, somewhat coarse, heavy. Leaflets dark glossy green curved or wrinkled at margins, giving them an irregularly cupped appearance;—margins sometimes lighter green in places blending back into leaflet along the veins;—serrations medium deep, blunt, broad, often double or notched, especially on lower margin of outside two leaflets. Leaflets mostly blunt at end not pointed, with an occasional middle leaflet more elongated with more of a pointed end. Leaflets average three inches long and two and one-half inches wide when fully developed. Stem of each leaflet medium short, giving whole leaf a condensed appearance. Mid-veins and others sunken below surface giving leaflets an oval raised surface between veins. Under surface of leaflets of a light frosted appearance with network of small veins showing up in a darker green;—mid-veins and side branches prominent, covered with light to white pubescence lying almost flat pointing outward.

*Leaf stems.*—Medium to heavy, averaging seven (7) inches long;—upright to spreading, green turning to reddish brown when exposed to sun. Pubescence medium heavy outspreading to drooping. Many of the leaf stems have one or two small "leaflets" near outer end,—about two-thirds way up to base of leaf. This is especially noticeable where soil is above average richness.

*Runners.*—Numerous, size medium to heavy, not slender or wiry, appearing before the end of the spring fruiting season and continuing to form from mother plant three to four weeks later in newly spring-set plantations. Distance between plants on runners averaging eight (8) to ten (10) inches. Distance between first and second runner plant on runner six (6) to eight (8) inches, other runner plants eight (8) to ten (10) inches apart on runners. Scale at internode prominent, often leaflike, from the axil of which branch runners are common. Occasionally there are two nodes found on runners between plants each supporting a scale, in the axil of which appears a bud. Pubescence numerous, outstanding to drooping backward toward base of plant. Color light green, reddish brown on upper surface when exposed to sun.

*Blossoms.*—Perfect, opening medium early to late during spring strawberry blossom period, appearing even with to just below leaves, occasionally, few blossoms appear during latter part of fruit ripening period;—average size three-fourths (¾) inch spread. Petals six (6) to eight (8) white with a light shade of green, slightly longer than wide somewhat cupped at margins on outer half, not pointed. Stamens numerous with bright yellow pollen sacs, borne on stout filament with length half to three-fourths as long as the immature berry (receptacle with its pistils);—pollen plentiful.

*Fruit stems.*—Medium to stout, erect to slightly spreading. First branching takes place between one-half to two-thirds total length of fruiting stem and cluster, the secondary and tertiary branches one to one and a inches, so that fruiting clusters are not condensed. Stems of individual berries one to one and a half inches long. On average stems all the primary, secondary, tertiary and occasionally the quarternary berries develop to marketable size.

*Fruit.*—Medium early with average to long picking season;—size, medium, uniform;—form conic to long conic, primaries more blunt conic, slightly depressed between shoulder and apex giving berry a shouldered appearance, others more uniformly conic;—color, dark crimson somewhat glossy, ripens evenly with uniform color;—flesh bright red all way through berry, subacid, solid and very firm, quality very good;—core same color as flesh, solid, tender, but firm;—calyx medium size, moderately adherent not necked, easily detached;—seeds, bright yellow, attractive, even with surface. Berries very firm and solid, holding their firmness, shape and color for forty-eight to seventy-two hours after picking. Shipping and canning qualities are the best.

What we desire to claim is:

The strawberry herein shown and described, characterized by its conic to large conic shape, its firmness, and its fine canning qualities.

BERT W. KEITH.
BUD H. KEITH.